US006705900B2

United States Patent
Sommer et al.

(10) Patent No.: US 6,705,900 B2
(45) Date of Patent: Mar. 16, 2004

(54) LEAD UP-SIZING SLEEVE

(75) Inventors: John L. Sommer, Coon Rapids, MN (US); Douglas S. Hine, White Bear Lake, MN (US); Vicki L. Bjorklund, Maple Grove, MN (US); Elisabeth Lacy Belden, Maple Grove, MN (US); William J. Clemens, Fridley, MN (US); Andrew J. Ries, Lino Lakes, MN (US); Jordon D. Honeck, Rogers, MN (US); Harry Schroder, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/838,814

(22) Filed: Apr. 19, 2001

(65) Prior Publication Data

US 2002/0115343 A1 Aug. 22, 2002

Related U.S. Application Data

(60) Provisional application No. 60/270,074, filed on Feb. 21, 2001.

(51) Int. Cl.[7] .................... H01R 24/04; H01R 13/627; H01R 13/52; H01R 4/36
(52) U.S. Cl. .................... 439/668; 439/359; 439/281; 439/814
(58) Field of Search ................. 439/668, 271, 439/281, 810, 814, 359, 651; 128/419

(56) References Cited

U.S. PATENT DOCUMENTS

| 4,411,277 A | * 10/1983 | Dickhudt .................... 439/593 |
| 4,583,543 A | 4/1986 | Peers-Trevarton |
| 4,628,934 A | 12/1986 | Pohndorf et al. |
| 4,740,170 A | 4/1988 | Lee et al. |
| 5,000,177 A | 3/1991 | Hoffmann et al. |
| 5,007,864 A | 4/1991 | Stutz, Jr. |
| 5,050,602 A | 9/1991 | Osypka |
| 5,060,649 A | 10/1991 | Höcherl et al. |
| 5,328,442 A | 7/1994 | Levine |
| 5,374,279 A | 12/1994 | Duffin, Jr. et al. |
| 5,439,391 A | 8/1995 | McEtchin et al. |
| 5,679,026 A | 10/1997 | Fain et al. |
| 5,697,804 A | 12/1997 | Froberg et al. |
| 5,760,341 A | 6/1998 | Laske et al. |
| 5,843,141 A | 12/1998 | Bischoff et al. |
| 6,044,302 A | 3/2000 | Persuitti et al. |

FOREIGN PATENT DOCUMENTS

EP 0442807 5/1998 .......... A61N/1/375

OTHER PUBLICATIONS

Medtronic Model 5866–45 Sizing Sleeve Technical Manual, Jan. 2002.
Medtronic Model 6925 Sizing Sleeve Kit Technical Manual, Oct. 1996.
Medtronic Model 6920 Sizing Sleeve Kit Technical Manual, Jan. 1997.

* cited by examiner

Primary Examiner—Chandrika Prasad
(74) Attorney, Agent, or Firm—Girma Wolde-Michael; Michael C. Soldner (57) ABSTRACT

An improved connection system for coupling a device such as a pacemaker, cardioverter, defibrillator, nerve stimulator, muscle stimulator, implantable monitor or other medical device to a medical lead is disclosed. The connection system includes a coupling member designed to couple to the proximal end of the lead. This coupling member, which includes an inner lumen sized to form a press fit around the proximal end of the lead body, may be of a generally tubular construction. This coupling member includes connector means to enable a connector pin at the proximal end of the lead to mechanically and electrically couple to a device. The connector means may further include means for coupling both mechanically and electrically to a ring connector on the proximal end of a multi-polar lead. An insertion member may also be provided to allow the lead to be more easily inserted within the inner lumen of the coupling member.

18 Claims, 12 Drawing Sheets

LEAD UP-SIZING SLEEVE

RELATED APPLICATIONS

This Application claims priority to provisionally-filed U.S. Patent Application Ser. No. 60/270,074 filed Feb. 21, 2001 entitled "Lead Up-Sizing Sleeve", which is incorporated herein by reference in its entirety.

FIELD OF THE INVENTION

The present invention relates generally to mechanisms for interconnecting electrical leads and electrical medical devices; and more particularly, to systems and methods of interconnecting implantable electrical leads and implantable medical electrical devices such as pacemakers, nerve stimulators, implantable defibrillators, implantable monitors, and so forth.

BACKGROUND OF THE INVENTION

As implantable electrical devices have increased in their complexity, there has been an increasing variety of electrical lead systems developed for use in conjunction with these devices. Nowhere is this more apparent than in the context of implantable cardioverter/defibrillators, which may include three, four, five, or more electrodes located on various numbers of implantable electrical leads. The leads themselves may carry one, two, three, or more electrodes, and may employ a variety of different electrical connector configurations and types. As a result, manufacturers of implantable cardioverter/defibrillators have had to produce their products with a variety of connector block configurations, capable of use with different lead systems. For example, Medtronic, Inc. presently manufactures implantable cardioverter/defibrillators with four basic connector designs, designated configurations "B", "C", "D", and "E". The "B" configuration includes three 6.5 mm connector bores for receiving high voltage electrical lead connectors of the type used to couple to cardioversion/defibrillation electrodes and one 3.2 mm in-line electrical connector bore compatible with the IS-1 connector standard for receiving an IS-1 electrical lead connector of the type generally used to couple to cardiac pacing and sensing electrodes. The "C" configuration includes a single 3.2 mm connector bore conforming to the DF-1 standard for receiving high voltage electrical lead connectors used to couple to cardioversion/defibrillation electrodes. This configuration also includes a single IS-1 connector bore. The "D" configuration includes three DF-1 connector bores and one IS-1 connector bore. The "E" configuration includes two 6.5 mm connector bores and two 5 mm connector bores for receiving electrical lead connectors used to couple to individual cardiac pacing and sensing electrodes.

As is apparent from the above discussion, multiple connectors block types are necessitated both by the use of multiple connector standards, and also because of the desire to connect a varying number of lead systems to a given device. The situation is complicated even further by the use of non-standard connector systems. For example, it has been increasingly common to utilize small-diameter guide catheters to deliver leads having a diameter of 7 French or less to a desired implant site. After lead placement is completed, the catheter must be withdrawn from the body. However, if the catheter has a small inner diameter, the inner lumen of the catheter cannot accommodate a standard-size lead connector such as one conforming to the IS-1 standard. In this situation, the catheter must be split or slit into two portions. Such slittable or splittable catheters are more expensive to manufacture, and require the additional slitting step to remove. To remedy this problem, the lead may instead include a small-diameter, non-standard connector that easily fits within the catheter lumen, allowing the catheter to be readily withdrawn from the body. This non-standard connector has the drawback of necessitating the use of an even larger number of connector block configurations.

One way to solve the problem is to provide adapters that adapt one lead connector type to a different connector type on the device. These adapters may take the form of a relatively short lead which at one end has a connector assembly which may be inserted into one or more bores on the connector block on the implantable device and at the other end has one or more connector bores capable of receiving the connector assembly or assemblies on the electrical leads to be used with the device. These adapters are bulky and add substantially to the size of the pocket in which the device is to be implanted. In addition, they tend to require a number of additional steps to be performed by the physician in order to couple the leads to the implanted device, and are thus seen as undesirable generally. Such adapters are disclosed in U.S. Pat. No. 5,000,177, issued to Hoffmann, and U.S. Pat. No. 5,328,442, issued to Levine. Some adapters, such as disclosed in U.S. Pat. Nos. 5,050,602 issued to Osypka and 5,060,649 issued to Hocherl et al. even required removal of the connector assembly of the lead as part of the connection process.

Another approach to resolving lead/device incompatibility problems involves use of an up-sizing adapter. An up-sizing adapter is used to convert a smaller-diameter standard or non-standard lead connector to a larger-sized device connector. This is particularly useful when dealing with leads having smaller connectors for use with non-splittable guide catheters. As discussed above, a smaller lead connector allows guide catheters to be easily withdrawn over the lead proximal end after the implant procedure is completed. After the guide catheter has been removed from the body, the up-sizing adapter may be connected to allow the lead to be coupled to a device.

One example of an up-sizing adapter is shown in U.S. Pat. No. 5,007,864, issued to Stutz Jr. This patent discloses an adapter to convert a smaller-diameter unipolar lead system to a larger connector block. Although this system allows a small-diameter lead to be used with a non-splittable catheter, this system has a disadvantage of not being adaptable for use with a bipolar leads.

Another example of an up-sizing adapter is disclosed in U.S. Pat. No. 4,583,543 issued to Peers-Trevarton. While this system is adaptable for use with bi-polar lead systems, it can only be used with a lead having a connector pin that is smaller than the connector bore. That is, it is not adaptable for use with a lead having a standard connector pin size but a non-standard connector body.

What is needed, therefore, is an improved system and method for allowing a lead connector of a first size to couple to a larger-sized device connector, and that addresses the foregoing problems.

SUMMARY OF THE INVENTION

The present invention is an improved connection system for coupling a device such as a pacemaker, cardioverter, defibrillator, nerve stimulator, muscle stimulator, implantable monitor or other device of the sort to a medical lead and which addresses the lead/device incompatibility issues discussed above while avoiding at least some of the drawbacks associated with conventional adapters or converters.

The current invention provides an up-sizing mechanism that may be used to size the proximal end of a lead to a predetermined convention such as the IS-1 standard. The system includes an up-sizing sleeve designed to couple to the proximal end of the lead, having a terminal connector pin conforming to a predetermined diameter, to a medical device. This up-sizing sleeve, which includes an internal surface forming a lumen sized to engage the proximal end of the lead and interior sealing rings to provide a fluid tight seal with the proximal end of the lead, may have one more relatively flexible and generally tubular members. The lead connector pin extends proximally beyond a proximal opening of the up-sizing sleeve, for a predetermined length, when the proximal end of the lead is engaged within the lumen of the up-sizing sleeve. Relatively rigid support members of the up-sizing sleeve prevent deformation of the sleeve, in order to maintain predetermined dimensions of an external surface of the sleeve when the proximal end of the lead is engaged within the lumen of the upsizing sleeve.

In another embodiment, the up-sizing sleeve includes a conductive ring member defining a means for electrically engaging to a ring connector on the proximal end of a lead. This means may include teeth for engaging the ring connector of the lead. Alternatively, the means may include a multi-beam connector or a spring coil. Furthermore, the conductive ring member of the up-sizing sleeve may be positioned between two relatively flexible and generally tubular members of the sleeve and include channels through which the two members are coupled. Additionally an alternative embodiment may include grommets, which serve as the interior sealing rings of the up-sizing sleeve, housed within the support members.

In additional embodiments many types of mechanical coupling mechanisms may be adapted to rigidly couple the up-sizing sleeve to the connector ring of the lead.

In a two-piece embodiment of the up-sizing sleeve, a first portion and second portion are adapted to come together in a snap fit. The conductive ring member is an integral part of the first portion, and the means for electrically engaging the connector ring of the proximal end of the lead is an integral part of the second portion. The means for electrical engagement is composed of deformable members adapted to slide under an edge of the conductive ring member for a snap fit within an inner surface of the conductive ring member.

In yet another embodiment of the current invention, one or more grooves may be formed in the proximal end of the lead and located to engage one or more positioning lips formed in the internal surface of the up-sizing sleeve when the proximal end of the lead is engaged within the lumen of the sleeve and the connector pin extends beyond a proximal opening of the sleeve for a predetermined length. Alternatively, the one or more grooves may engage one or more sealing rings of the up-sizing sleeve in a similar fashion.

In one embodiment, the up-sizing sleeve includes a reinforcing structure such as a coil. This reinforcing structure prevents the lead from flexing in a manner that results in lead failures. The coupling member may further include sealing rings on the exterior surface to provide a fluid-tight seal with the medical device, and/or sealing rings within the inner lumen to provide a fluid-tight seal with the lead body.

Because of the relatively tight press-fit formed between the up-sizing sleeve and the proximal end of the lead, one embodiment of the system includes a means to allow the lead to be more easily inserted within the inner lumen of the up-sizing sleeve. In one embodiment, the means to aid in insertion is a pull-wire device adapted to pull the proximal end of a medical electrical lead into the lumen of the up-sizing sleeve. Force applied to the pull wire pulls the lead body into the lumen of the sleeve until the connector pin extends proximally for a predetermined length beyond the proximal opening of the sleeve. In a second embodiment, the means to aid in insertion is a split tube that is inserted into a distal opening of the up-sizing sleeve. The proximal end of the lead is inserted into the lumen of the up-sizing sleeve via the split tube, which is then removed from around the lead body and extracted from the lumen of the up-sizing sleeve.

According to yet another embodiment of the current system, the up-sizing sleeve is bifurcated, having an offset leg to adapt the proximal end of a lead to more than one predetermined convention or standard. For example, the bifurcated up-sizing sleeve may conform to both a DF-1 and IS-1 standard.

The up-sizing system of the current invention provides a mechanism for up-sizing a lead having a non-standard proximal end terminated in a connector pin having a standard diameter. For example, the invention is particularly suited for small-diameter leads having an in-line connector pin. Unlike prior art designs, the up-sizing sleeve of the current invention allows the connector pin of the lead to be coupled directly to a medical device, while providing a means to up-size the proximal end of the lead body. Other advantages of the inventive connection system will become apparent to those skilled in the art from the drawings and accompanying description.

DETAILED DESCRIPTION OF THE PREFERRED EMBODIMENTS

Figure 1A:
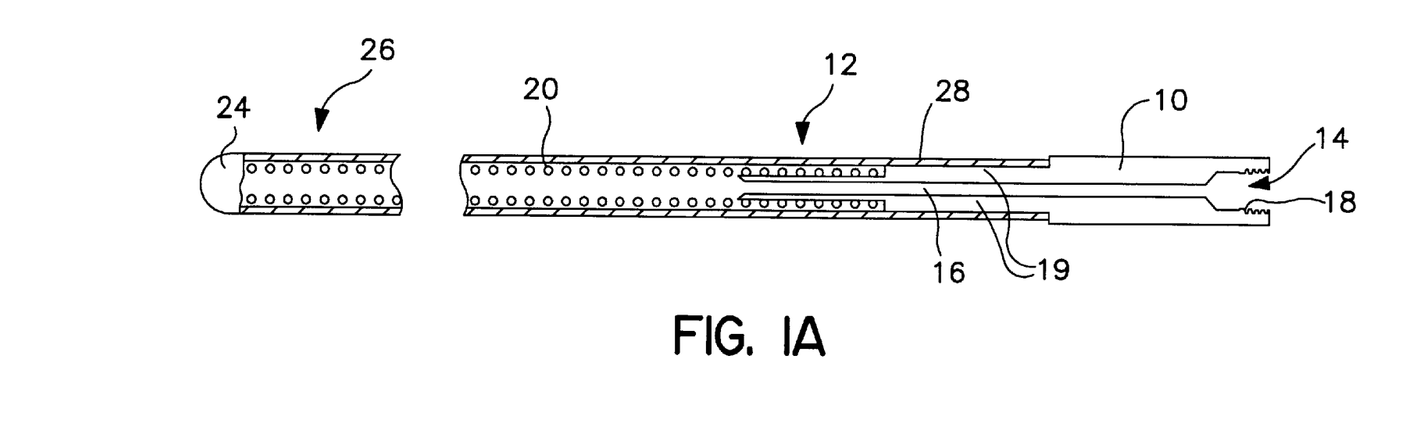
FIG. 1A is a side cutaway view of an exemplary unipolar lead connector of the type that may be employed with the current inventive system.

FIG. 1A is a side cutaway view of an exemplary unipolar lead connector of the type that may be employed with the current inventive system. The lead includes a connector pin 10 at the proximal end of the lead. In this view, the connector pin has substantially the same diameter as the lead body 12, although this is not necessary. Connector pin has an opening 14 that extends to inner lumen 16. A portion 18 of inner lumen 16 may be threaded.

Connector pin 10 couples to conductive member 19 that extends into lumen 16 and is electrically and mechanically coupled to at least one conductor 20. In FIG. 1A, conductor 20 is a conductive coil that extends the length of the lead body 12 to a tip electrode 24 at the lead body distal tip 26. In other embodiments, conductor 20 may take the form of a single-filar or multi-filar stranded conductor.

Lead body further includes an insulative jacket 28 that may be formed of a biocompatible polymer such as polyurethane or silicone. It may be noted that the lead of FIG. 1A is merely exemplary, and many other leads may be employed with the current invention. For example, a lead without an inner lumen extending within lead body 12 may be utilized. Alternatively, having multiple inner lumens may likewise be utilized.

Figure 1B:
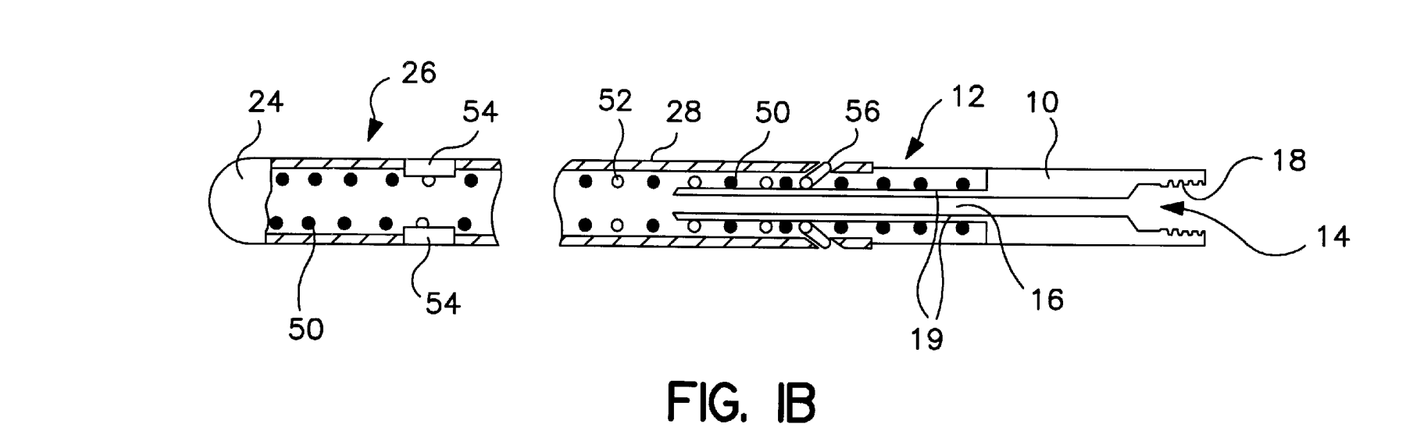
FIG. 1B is a side cutaway view of an exemplary bipolar lead connector of the type that may be employed with the current inventive system.

FIG. 1B is a side cutaway view of an exemplary bipolar lead connector of the type that may be employed with the current inventive system. In FIG. 1B, elements that are similar to those shown in FIG. 1A are labeled with like designators. The lead of FIG. 1B includes a connector pin 10 that couples to conductive member 19. Conductive member 19 is electrically and mechanically coupled to an insulated coiled conductor 50. This conductor 50 extends the length of lead body 12 and is coupled at the distal tip 26 to tip electrode 24. A second insulated coiled conductor 52 is also provided to couple ring electrode 54 at the lead distal end to ring connector 56. In another embodiment, the conductors may be single or multi-filar stranded conductors.

Figure 1C:
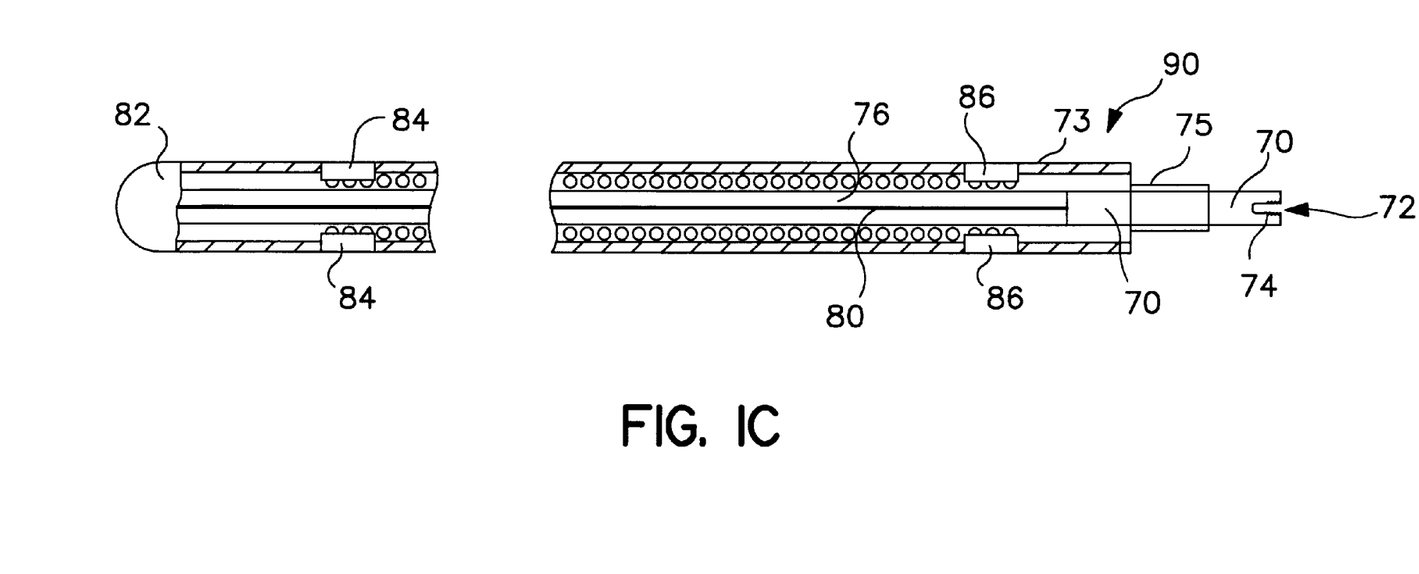
FIG. 1C is a side cutaway view of yet another exemplary bipolar lead connector of the type that may be employed with the current inventive system.

FIG. 1C is a side cutaway view of yet another exemplary bipolar lead connector of the type that may be employed with the current inventive system. In this embodiment, a connector pin 70 is shown having an opening 72 that includes an inner, threaded surface 74. A portion of the connector pin is shown surrounded by an insulative sleeve 75 which may be formed of a polymer. This insulative sleeve electrically isolates pin from a connector ring 73, and provides additional structural support. The connector pin, which may have dimensions conforming to an IS-1 or another standard, extends within an inner lumen 76 of the lead body 12. This inner lumen houses a stranded conductor 80 such as shown in commonly-assigned U.S. Pat. No. 5,760,341 that is electrically coupled to tip electrode 82. The conductor 80 may be a single or multi-filar stranded conductor, or in a different embodiment, may be a coiled conductor. A second, coiled conductor 84 electrically couples ring electrode 86 to connector ring 73. It may be noted that although the connector pin 70 of this design may be of a dimension that corresponds to a standard such as an IS-1 connector pin standard, the overall lead dimensions of the proximal end 90 of the lead do not necessarily conform to any standard.

As discussed above, the lead configurations shown in FIGS. 1A, 1B, and 1C have small connector profiles. Therefore, a guide catheter used to place the leads during an implant procedure may be readily withdrawn over the connector pin without having to split or slit the catheter body. However, because of the small connector profiles, all dimensions of the connector pin 70 and the proximal end 90 of the lead body do not conform to a connector standard such as IS-1 , making connection to a standard device connector block difficult. The upsizing sleeve of the current invention is provided as a means for facilitating this connection so that a specialized device connector block is not needed.

Figure 2A:
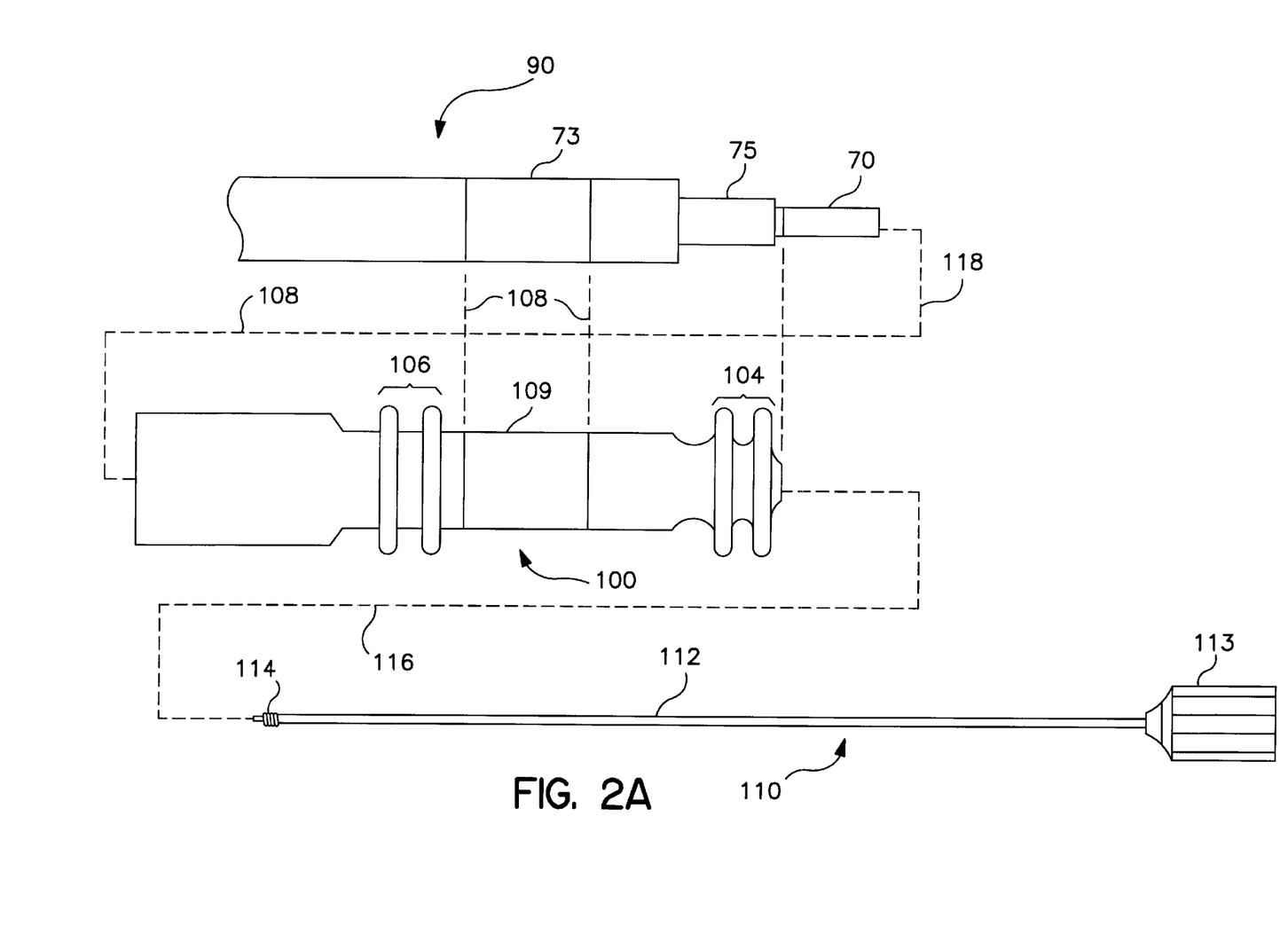
FIG. 2A is a plan view of one embodiment of an upsizing sleeve according to the current invention.

FIG. 2A is a plan view of one embodiment of an upsizing sleeve 100 according to the current invention. This upsizing sleeve is a generally tubular member having an inner lumen (not shown in FIG. 2) that is adapted to receive the proximal end of a lead such as the lead shown in FIG. 1C. The inner lumen of the upsizing sleeve is slightly larger than the outer diameter of proximal end 90 of the lead. For example, the proximal end 90 of the lead of FIG. 1C may be adapted to fit within the inner lumen as indicated by dashed line 102 such that the lead body forms a press fit with the surface defined by the lumen. The upsizing sleeve is adapted to conform to a standard configuration such as an IS-1 standard.

Upsizing sleeve is shown to include two sets of exterior sealing rings 104 and 106 adapted to sealingly engage with the connector port of a device such as pacemaker or defibrillator. Upsizing sleeve further includes a conductive ring member 109 adapted to electrically couple to connector ring 73 of the lead, as shown by dashed lines 108 in a manner to be discussed further below. Conductive ring member 109 is further adapted to mechanically and electrically couple to a set screw within the device connector to thereby couple ring connector 73 to a medical device in a manner dictated by the IS-1 connector standard. Sealing rings and the portions of upsizing sleeves surrounding conductive ring member 109 may be formed of one or more polymer structures such as polyurethane or silicone in a manner to be discussed further below.

Because of the relatively tight press-fit between the proximal end 90 of the lead and the upsizing sleeve 100, a pull-wire device 110 may be provided to aid in the insertion process. One embodiment of the pull-wire device 110 includes a rigid pull-wire 112 and a handle 113. The rigid pull-wire 112 may include a threaded distal end 114, which is inserted through the inner lumen of upsizing sleeve 100, as shown by dashed line 116. The threads of threaded distal end 114 are then positioned to engage threaded surface 74 (FIG. 1C) of the connector pin 70, as shown by dashed line 118. This allows the pull-wire 112 to rigidly engage the proximal end 90 of the lead so that the lead may be pulled through the inner lumen of the upsizing sleeve 100.

Although FIG. 2A shows pull-wire 112 including threaded distal end 114 to engage a lead, other coupling means could be provided to coupled to the lead, including a spring-loaded clip, or a plug to form a press-fit with opening 72.

Figure 2B:
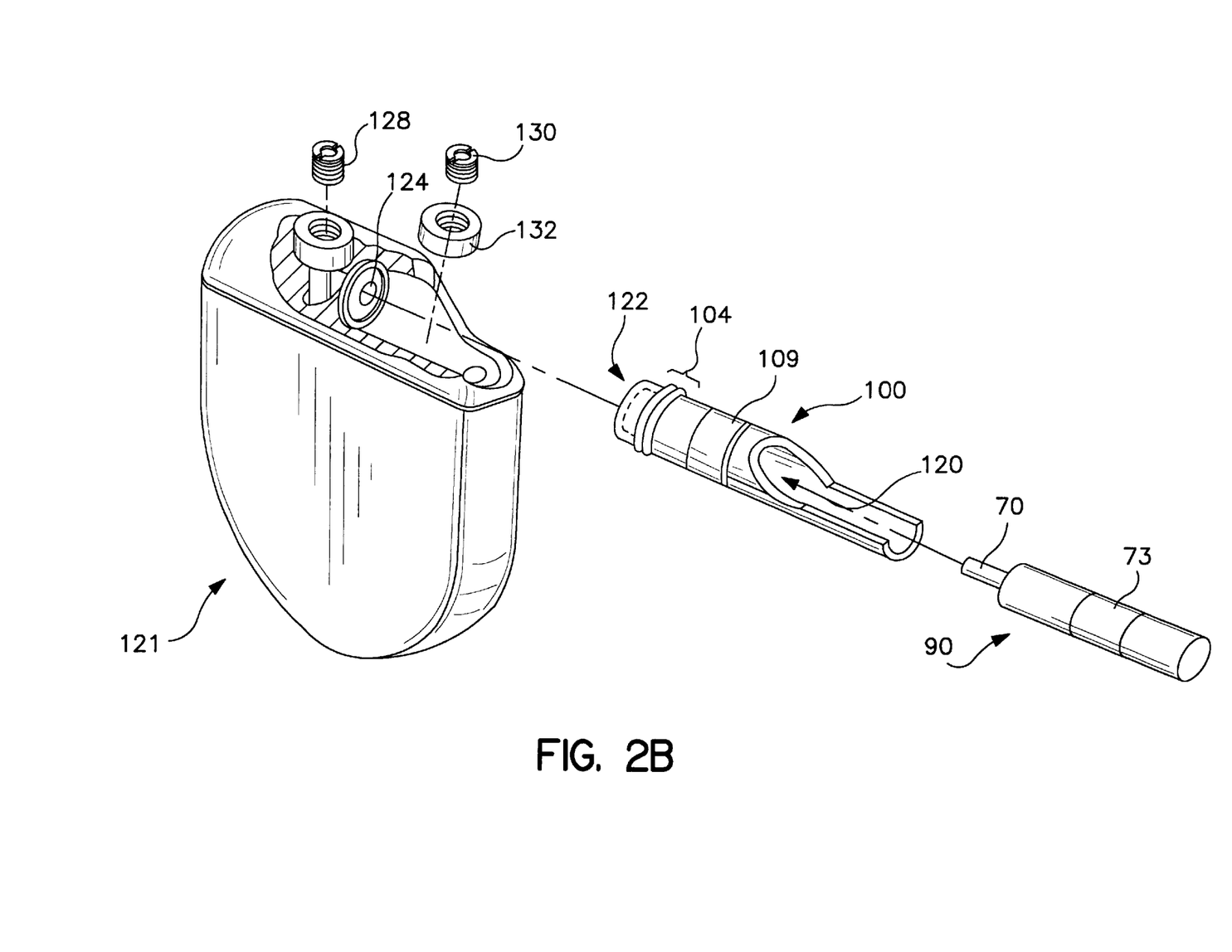
FIG. 2B is a perspective view illustrating the manner in which the inventive upsizing sleeve may be used to couple a lead to a medical device.

FIG. 2B is a perspective view illustrating the manner in which the inventive up-sizing sleeve may be used to couple a lead to a medical device. The proximal end 90 of a lead such as shown in FIG. 1C includes a connector pin 70 and connector ring 73. This lead may be inserted into the inner lumen 120 of sleeve 100 so that connector ring 73 forms a press fit with conductive ring member 109, with connector pin 70 extending through the proximal end 122 of the sleeve. Connector pin is adapted to be received by port 124 of the medical device 121, which is further maintained by set-screw 128. A second set-screw 130 and washer 132 is provided to form a connection with conductive ring member 109.

Figure 3:
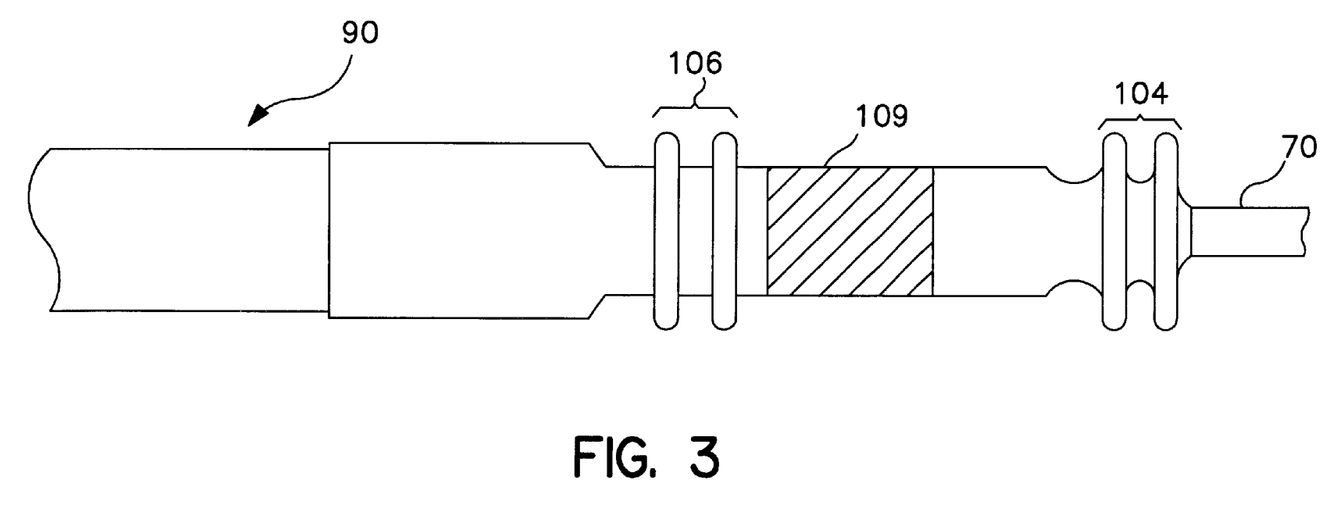
FIG. 3 is a plan view illustrating proximal end of the lead of FIG. 1C inserted within upsizing sleeve.

FIG. 3 is a plan view illustrating proximal end 90 of the lead of FIG. 1C inserted within upsizing sleeve 100. Connector pin 70 extends through the proximal end of the upsizing sleeve, whereas the lead body of proximal end extends out the distal end of the upsizing sleeve.

Figure 4A:
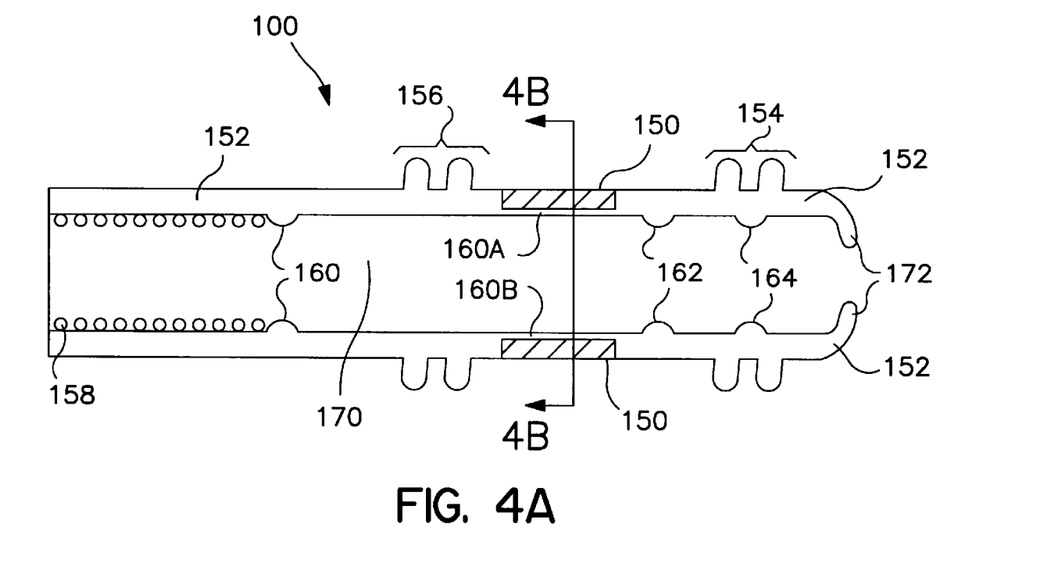
FIG. 4A is a side cutaway view of one embodiment of the upsizing sleeve of the current invention that may be formed using an over-molding process.

FIG. 4A is a side cutaway view of one embodiment of upsizing sleeve 100. A conductive ring member 150 is provided to couple to a connector ring such as connector ring 73 (FIG. 1C) of a lead in the manner discussed above. This ring member may be formed of any conductive material such as a stainless steel, for example. The remainder of the upsizing sleeve is an integral structure 152 that includes sealing rings 154 and 156. This structure may be formed of a biocompatible polymer such as silicone using a silicone over-molding process as is known in the art. According to one aspect of the invention, the upsizing sleeve may be reinforced at the distal end with a reinforcing member 158 that may be formed of an insulative coil such as a PTFE coil, a conductor coil that may or may not be insulated, or any other material having strength properties that make it suitable for this purpose. This reinforcing member provides added support to prevent the lead proximal end 90 (FIG. 3) from flexing in a manner that may cause lead failures over time. In another embodiment, a reinforcing, tubular sleeve member may be inserted within the distal end of the upsizing sleeve to provide this type of support.

Upsizing sleeve may further include interior sealing rings within the inner lumen 170. For example, upsizing sleeve of FIG. 4A includes sealing rings 160, 162 and 164 to provide a fluid-tight seal with a lead inserted within inner lumen 170. Finally, upsizing sleeve is also show to have a lip 172 at the proximal end which may be provided to engage a corresponding structure on the lead. In this manner, upsizing sleeve is positioned over the lead so that connector pin 70 extends beyond the proximal end of upsizing sleeve 100 a predetermined distance that conforms to a given connector standard. For example, lip 172 may be adapted to engage the ridge formed by insulative sleeve 75 where the insulative sleeve meets the connector 70 (FIG. 1C).

Figure 4B:
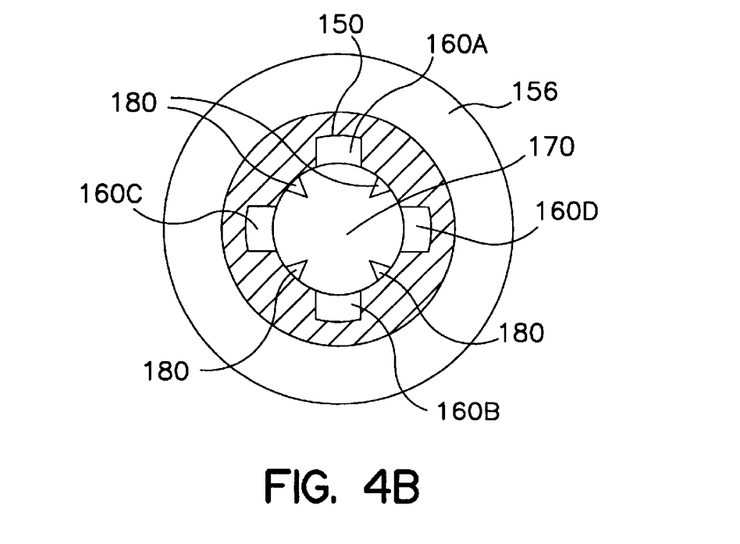
FIG. 4B is a cross-sectional view of upsizing sleeve at line 4B—4B of FIG. 4A.

FIG. 4B is a cross-sectional view of upsizing sleeve at line 4B—4B of FIG. 4A. This view shows conductive ring member 150 including channels adapted to receive a polymer during an over-molding process such as a silicone over-molding process discussed above. The flow of a polymer into these channels results in the formation of the connecting polymer structures 160A, 160B, 160C, and 160D. FIG. 4B further illustrates conductive teeth members 180 coupled to, or integrally formed, in conductive ring member 150. These conductive teeth members are adapted to engage a conductive ring of a lead such as connector ring 73 to form a more robust electrical connection between the connector ring and conductive ring member 150. This view further illustrates sealing rings 156.

Although teeth members 180 are shown in FIG. 4B to couple conductive ring member to a connector ring of a lead, many other mechanisms may be used in the alternative. For example, a keyed mechanism such as a woodruff or spline key may be used to lock a lead ring connector to the conductive ring member. Alternatively, a threaded aperture may be provided in the connective ring member so that a set-screw from a device connector block may be used to affix the sleeve to the lead via the threaded aperture. In yet another embodiment, small ports may be provided in the conductive ring member to receive conductive adhesive to enhance the electrical and mechanical contact between the conductive ring member and the lead ring connector. Alternatively, a hole in the conductive ring member may be aligned with a corresponding hole or groove in the lead so that a pin or rivet can be inserted to form a mechanical and electrical coupling. A thumb-actuated spring and ball-detent mechanism could be used to couple the sleeve to the lead. Another embodiment may include a thumb-activated push-collar such as is provided on steerable stylet handles. Any other type of coupling mechanisms may be used to form a stable electrical and mechanical fit between the conductive ring member and the connector ring of a lead.

Figure 5:
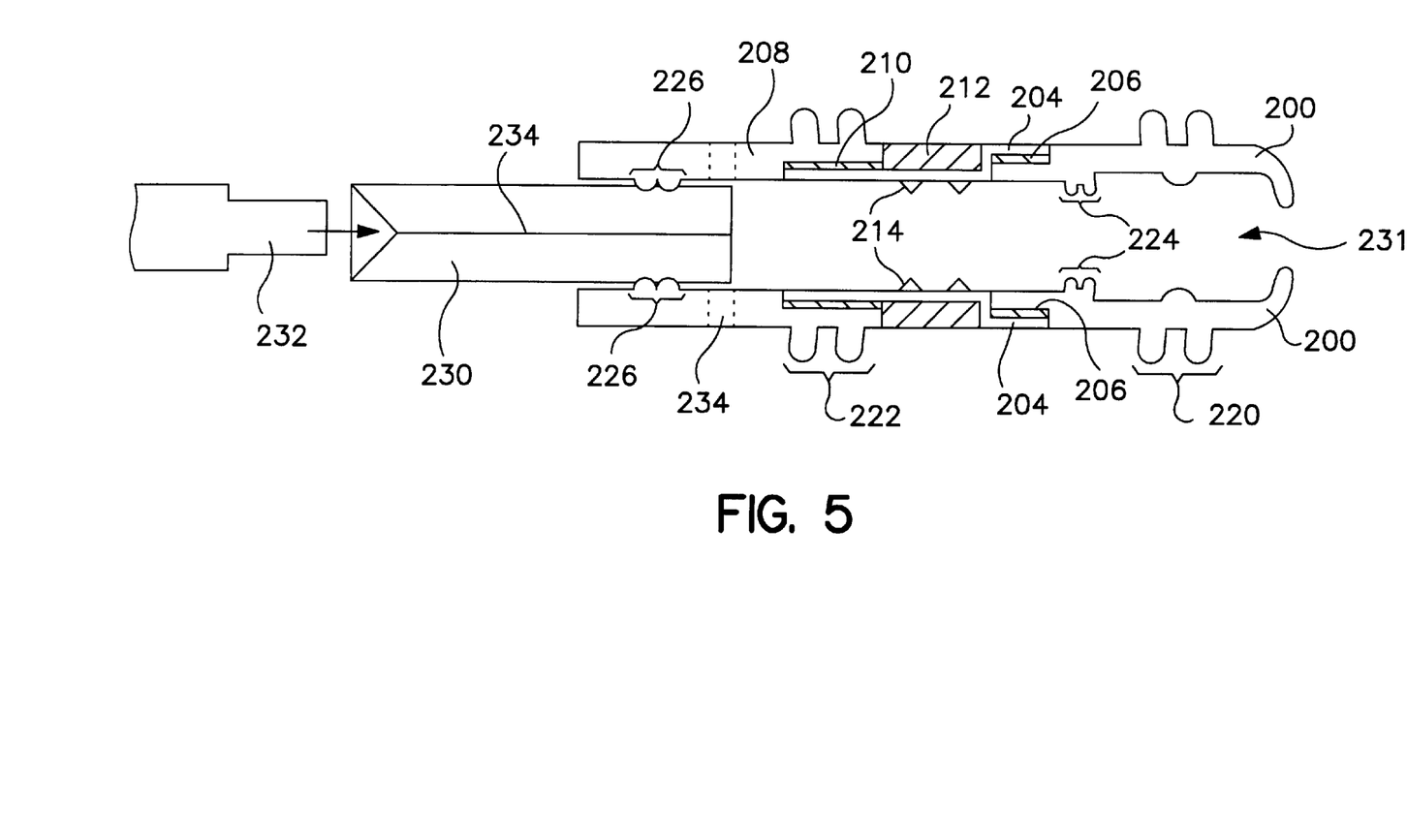
FIG. 5 is a cutaway side view of another embodiment of the upsizing sleeve of the current invention.

FIG. 5 is a cutaway side view of another embodiment of the upsizing sleeve of the current invention. In this embodiment, a first generally tubular member 200 which may be formed of silicone is bonded to a support member 204 using a first layer 206 of medical-grade adhesive. Support member, which may be formed of a material that is more rigid than the silicone such as a higher durometer polyurethane, is also bonded via adhesive layer 210 to a second generally tubular member 208, which may also be silicone. The support member 204 is adapted to provide additional structural rigidity that is not provided by a sleeve formed entirely of a lower-durometer material such as silicone. This rigidity is important to maintain precise sleeve dimensions so that the sleeve maintains a form that conforms to a predetermined standard even after undergoing the strain of forming a press fit with a lead.

A conductive ring member 212 surrounds the support member 204 and is adapted to engage a set-screw of a medical device as is provided on a standard IS-1 device connector block. In one embodiment, the conductive ring member 212 includes teeth 214 that extend through the support member to engage a connector ring of a bipolar lead. If a unipolar lead is to be employed, these teeth need not be included in the sleeve, since the ring connector of the lead need not make an electrical connection with a device connector block.

Each of tubular members 200 and 208 includes exterior sealing rings 220 and 222, respectively, to provide a fluid-tight seal with a device connector block. Each of the tubular members further includes interior sealing rings 224 and 226, respectively, to provide the fluid tight seal with a lead. As discussed above, preferably tubular members 200 and 208 are formed of a less rigid material such as silicone so that these sealing rings are more deformable and better able to provide a seal.

FIG. 5 also illustrates an alternative mechanism that may be used to engage a lead with the sleeve. A split tubular member composed of a material having a lubricious surface such as PTFE tubing 230 may be inserted in the distal end of the sleeve. The lubricious outer surface of the tubing allows the tubing 230 to be readily inserted into inner lumen 231 of the sleeve. A lead 232 may then be inserted within the inner lumen of the tubing 230 and the tubing removed. The slit 234 in the tubing allows it to be removed from around the lead after the lead is attached to the up-sizing sleeve. The use of this split tubular member thereby provides an alternative to the pull-wire tool (FIG. 2) as an aid to forming the press fit between a lead and the sleeve.

In one embodiment, sleeve may include one or more ports such as port 234 (shown dashed) to allow a medical-grade adhesive to be infused or injected between the sleeve and the lead after the lead is inserted into the sleeve to thereby secure the lead to the sleeve.

Figure 6:
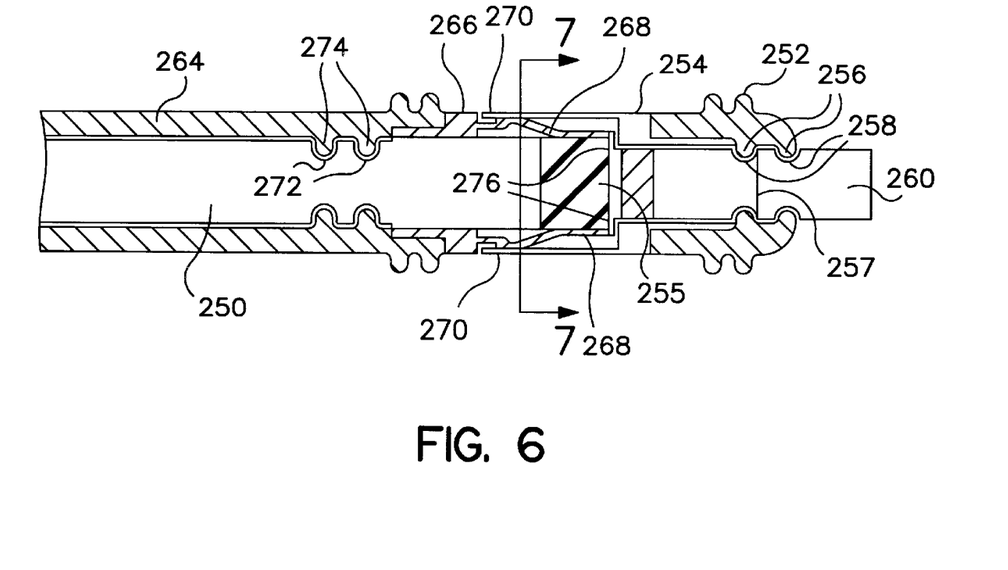
FIG. 6 is a cutaway side view of a two-piece sleeve member that may be assembled over the lead at the time of use.

FIG. 6 is a cutaway side view of a two-piece sleeve member that may be assembled over a lead such as lead 250 at the time of use. A first portion of the sleeve includes a less rigid, generally tubular member 252 that may be formed of silicon, and which is bonded to a conductive ring 254 via a medical-grade adhesive. Conductive ring 254, which is formed of a conductive material, is adapted to electrically and mechanically couple to a connector ring 255 of lead 250 via a second portion of the sleeve, as will be discussed further below. Conductive ring is further adapted to electrically couple to a connector block of a medical device, as may be accomplished using a set-screw.

In one embodiment, the tubular member 252 includes one or more lips 256 to engage grooved members 258 in the lead connector pin 260. This allows the sleeve to be seated over the lead so that the dimensions of the assembly conform to a predetermined standard such as IS-1. Lips 256 further provides a fluid-tight seal with lead 250. One of the lips 256 is shown interfacing with a seal zone 257 of the inline connector. As discussed above, tubular member 252 may be formed of a less rigid material such as silicone to provide sealing rings that allow for a better fluid-tight seal.

The two-piece sleeve of FIG. 6 further includes a second portion that is formed of a second less-rigid tubular member 264 such as silicone. Tubular member 264 is bonded to a connector member 266, which may be formed of a metal. Connector member 266 has deformable fingers 268 that slide under edge 270 to engage conductive ring 254 in a snap-fit that provides both a mechanical and electrical coupling between connector member 266 and conductive ring 254. Deformable fingers 268 also electrically couple to connector ring 255 of lead 250 so that an electrical connection is formed between the connector ring 255 and conductive ring 254 of the two-piece sleeve. This allows the connector ring 255 of lead 250 to be coupled to a connector block of a device via conductive ring 254.

The lead 250 of FIG. 6 may include grooves 272 to engage inner sealing rings 274, and may further having a shoulder 276 to engage conductive ring 254 in a manner that further allows the lead to seat in a position that conforms to a predetermined standard.

Figure 7:
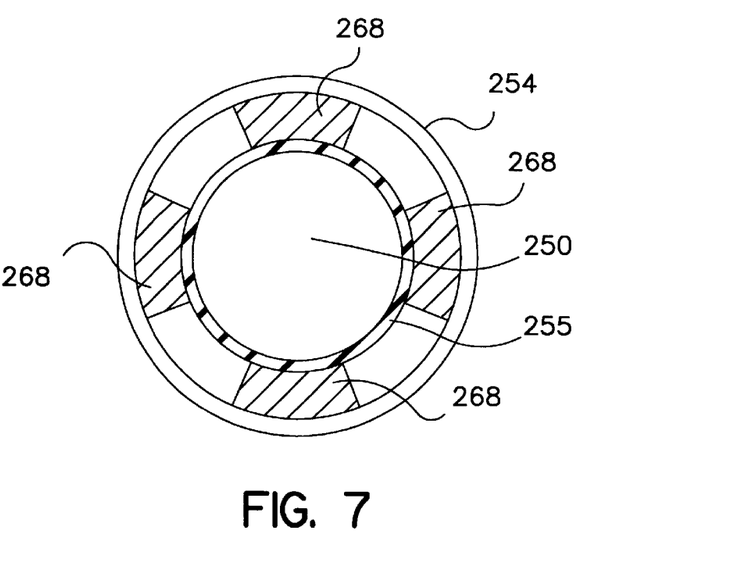
FIG. 7 is a cross-sectional view of the sleeve of FIG. 6 at line 7—7.

FIG. 7 is a cross-sectional view of the sleeve of FIG. 6 at line 7—7. This view shows the deformable fingers 268 electrically and mechanically engaging conductive ring 254, and further electrically engaging connector ring 255 of lead 250.

Figure 8:
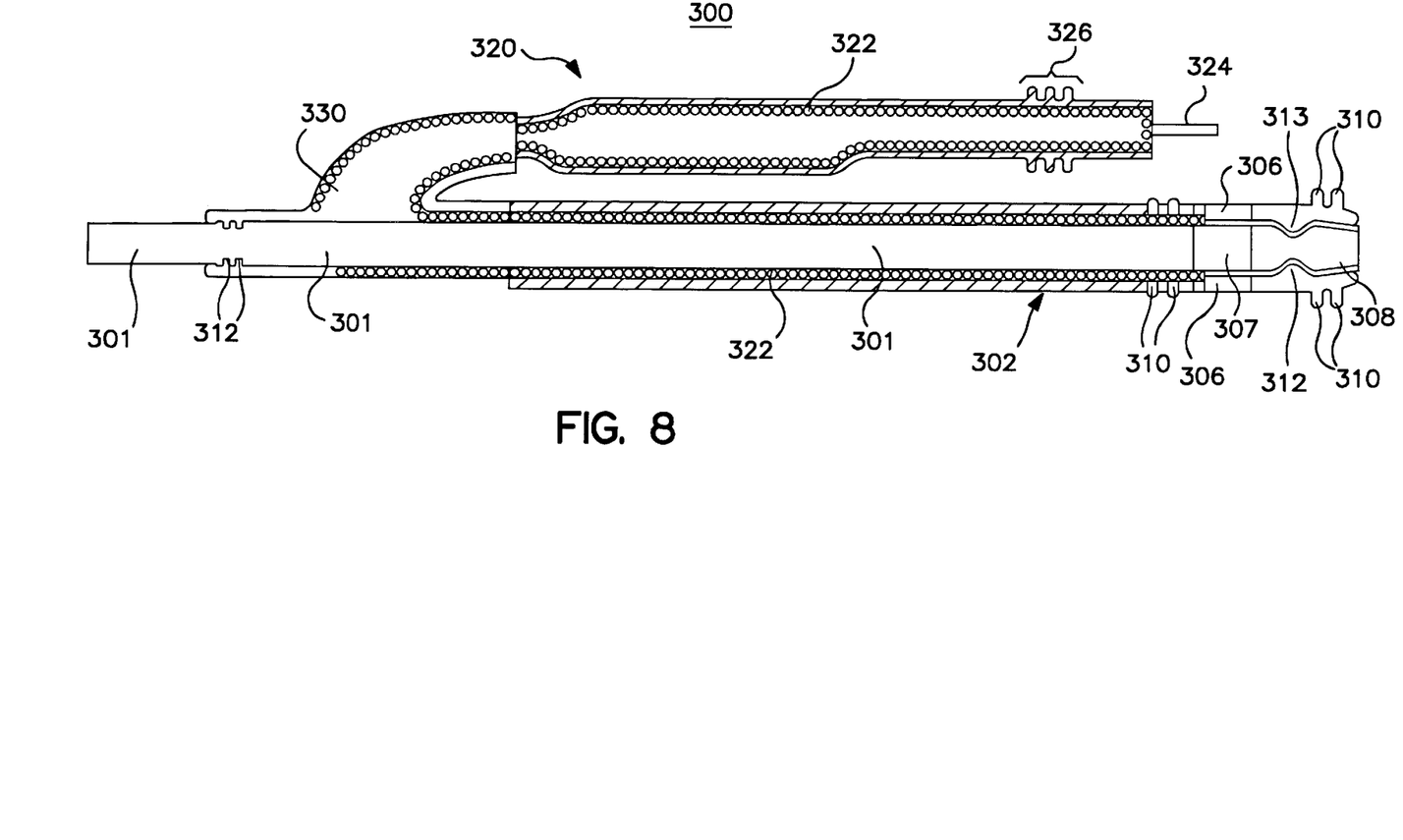
FIG. 8 is a cutaway side view of a bifurcated sleeve that includes two different connector standards.

FIG. 8 is a cutaway side view of a bifurcated sleeve 300 designed to adapt a lead to conform to two different connector standards. In the embodiment illustrated, lead 301 is shown engaging a first bifurcation leg 302 of the bifurcated sleeve that conforms to the IS-1 standard. This portion of the sleeve may be of any of the embodiments discussed above. A conductive ring member 306 is provided on bifurcation leg 302 to engage with a connector ring 307 of lead 301, and to further engage a connector block of a medical device in the manner discussed above. The pin 308 of the lead extends through the sleeve as discussed above, and exterior sealing rings 310 provide a fluid-tight fit with the medical device. Interior sealing rings 312 and 313 provide a fluid-tight fit with lead 301. Additional inner sealing rings (not shown) are provided to engage the proximal end of the lead as discussed above.

In this embodiment, pacing and sensing of a patient may be accomplished via ring connector 306 and pin 308 connectors, which coupled to tip and ring electrodes (not shown in FIG. 8), respectively, at the lead tip. Further assume the lead carries a high-voltage coil electrode that is electrically coupled to ring connector 306. An offset bifurcation leg 320 may then be used to provide a connector for cardioversion/defibrillation purposes. A high-voltage defibrillation coil 322 connects conductive ring member 306 with a connector pin 324 that may conform to a second standard such as a DF-1 standard. This connector pin 324 may be utilized by a medical device to deliver a cardioversion/defibrillation shock that is then carried via coil 322 and conductive ring member 306 to conductor ring 307, and finally to the defibrillation coil electrode as the proximal end of the lead. This embodiment of the sleeve thereby allows a bipolar lead having a pace/sense electrode pair and a single shock coil to be adapted to both IS-1 and DF-1 connector blocks without the need to slit or split a catheter that is used during lead delivery. Additionally, the current inventive sleeve eliminates the pocket bulk associated with traditional longitudinal adaptors.

Sleeve 300 may be formed of one or more biocompatible polymers. For example, the hub portion 330 of the bifurcated sleeve could be formed of a more rigid material such as polyurethane that provides additional support to the structure and to the proximal end of the lead. The remainder of the sleeve, including the portions of the legs 302 and 320 that include the exterior sealing rings 310 and 326, could be formed of a less rigid material such as silicone.

As noted above, the current inventive up-sizing sleeve is, in its preferred embodiment, designed to conform a lead to a predetermined connector standard. For this reason, it is important that the sleeve does not stretch or deform in any manner. To provide a structure that maintains precise dimensions, more rigid support structures formed of a material such as polyurethane may be incorporated into the sleeve. The inclusion of additional sealing grommets may also be desirable to ensure both a fluid-tight seal, and the retention of predetermined sleeve dimensions.

Figure 9:
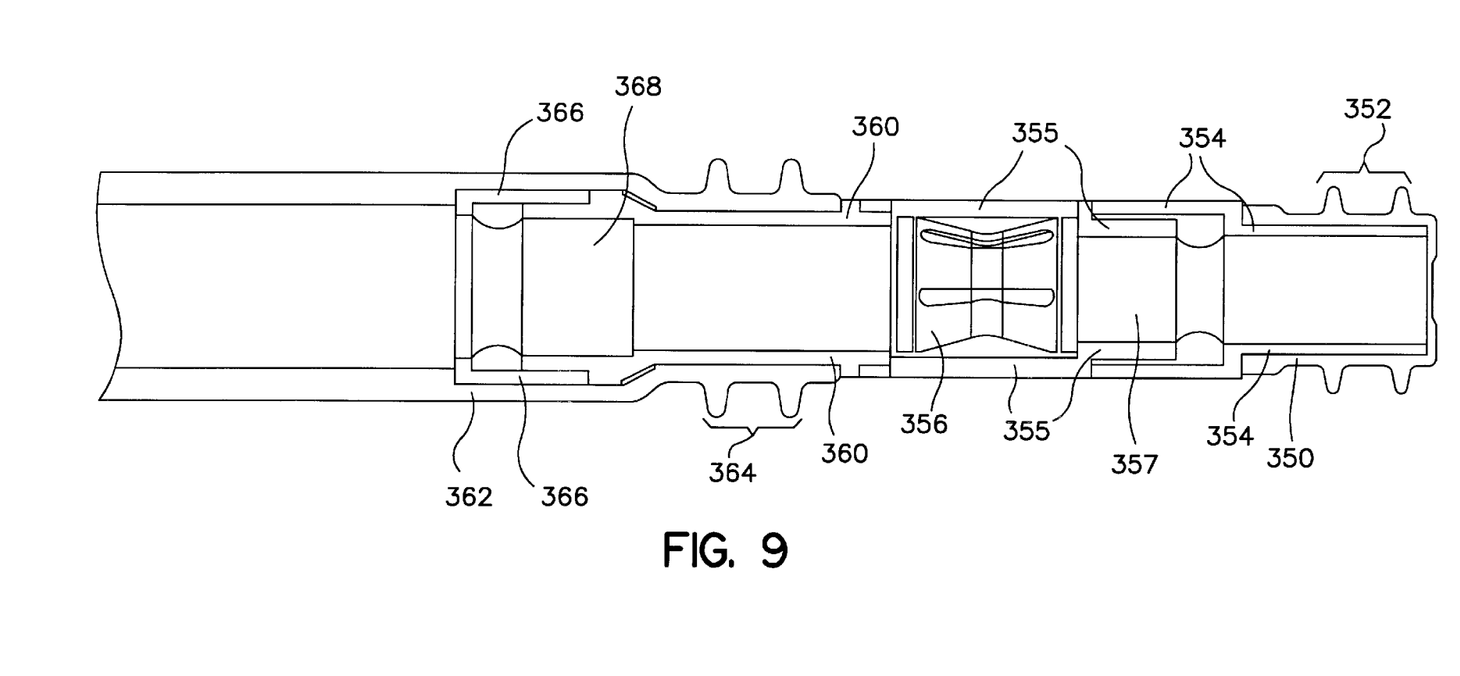
FIG. 9 is a side cutaway view of another embodiment of the current invention that incorporates both support structures and sealing grommets.

FIG. 9 is a side cutaway view of another embodiment of the current inventive up-sizing sleeve that incorporates both support structures and sealing grommets. A first, less-rigid tubular sleeve member 350 is shown having exterior sealing rings 352 as discussed above. Tubular member 350, which may be formed of a silicone, is bonded to a more rigid tubular support member 354, which may be formed of a polyurethane. Support member 354, is, in turn, coupled at one end to an exterior conductive ring 355 formed of an electrically-conductive material that is adapted to make an electrical connection with a connector block of a medical device, as is provided by a standard IS-1 connector.

Conductive ring 355 houses, and is mechanically and electrically coupled to, a connector member 356 that is also formed of a conductive material. Connector member 356 is adapted to make an electrical and mechanical connection with a connector ring of a lead in a manner similar to that discussed above. Connector member 356 is shown in this embodiment to be a multi-beam connector having deformable fingers adapted to form a press-fit with a lead connector ring. Alternatively, connector member 356 may take the form of any other type of connector known in the art, including any of the types of connectors discussed above.

Housed within conductive ring 354 may be a sealing grommet 357 provided to form a superior fluid-tight seal with a lead. Sealing grommet 357 may be formed of a more deformable material such a silicone, for example.

Conductive ring 355 is further bonded or welded to a second rigid tubular support member 360, which may be formed of a polyurethane or a metal. This second tubular support member 360 is also mechanically coupled to a less rigid, tubular sleeve member 362 having sealing rings 364, and which may be formed of silicone. Tubular support member 360 is bonded to a lip member 366 adapted to house a second sealing grommet 368. Lip member 366 may be formed of a rigid polymer such as a polyurethane, whereas the sealing grommet may be formed of silicone.

The embodiment shown in FIG. 9 provides a more flexible design. The length of the sealing grommets may be adjusted to position the conductive ring 355 based on a selected connector standard. Moreover, the multi-beam connector shown as connector member 356 may be adjusted to couple to any lead size requirement. This design is adaptable for over-the-wire leads, and small coil-over-cable leads having an outer diameter of 5 French or less.

It may be noted that while the multi-beam connector 356 of FIG. 9 may be adapted to form an electrical connection with a connector ring of a multi-polar lead, this need not be the case. In one embodiment, the multi-beam connector 356 may be formed of a non-conductive material. In this case, the connector 356 is adapted to form a mechanical connection with a unipolar lead so that the lead body is maintained in a stable position with respect to the up-sizing sleeve. In this embodiment, conductive ring 355 may be omitted if desired, or a similar structure may be provided that is formed of a non-conductive material.

Figure 10A:
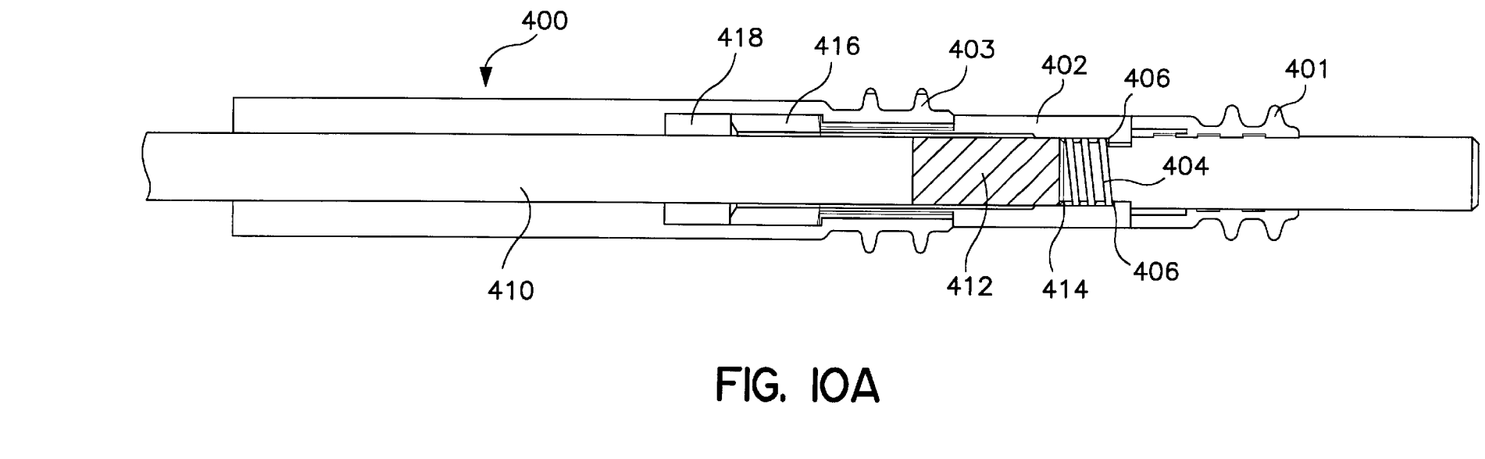
FIG. 10A is a side cutaway view showing an embodiment of the up-sizing sleeve that includes a spring coil to form the electrical connection between a lead ring connector and a conductive ring member of the upsizing sleeve.

FIG. 10A is a side cutaway view showing yet another embodiment of the up-sizing sleeve that includes a spring coil to form the electrical connection between a lead ring connector and a conductive ring member of the upsizing sleeve 400. Up-sizing sleeve 400 includes many of the components described above with respect to other ones of the embodiments of the invention. For example, the embodiment of FIG. 10A includes flexible tubular members 401 and 403 which may be formed of a silicone, and which are coupled as with a medical-grade adhesive to an electrically-conductive ring member 402. Most notably, in this embodiment, conductive ring member 402 is electrically and mechanically coupled at one end to a deformable spring coil 404. Spring coil 404, which is formed of an electrically-conductive material, may be spot welded or otherwise coupled to a shoulder 406 of conductive ring member 402. In this embodiment, lead 410 includes a ring conductor 412 having a lip 414 to engage spring coil 404. In this manner, ring connector 412 is electrically coupled to the conductive ring member 402, which, in turn, may be coupled to the connector block of a medical device. The upsizing sleeve may further include one or more grommets such as grommet 416, which is maintained in position by a polyurethane lip member 418 similar to that shown in the embodiment of FIG. 9. The upsizing sleeve may further include other aspects described with respect to the embodiments of FIGS. 1–9 as would be apparent to those skilled in the art.

Figure 10B:
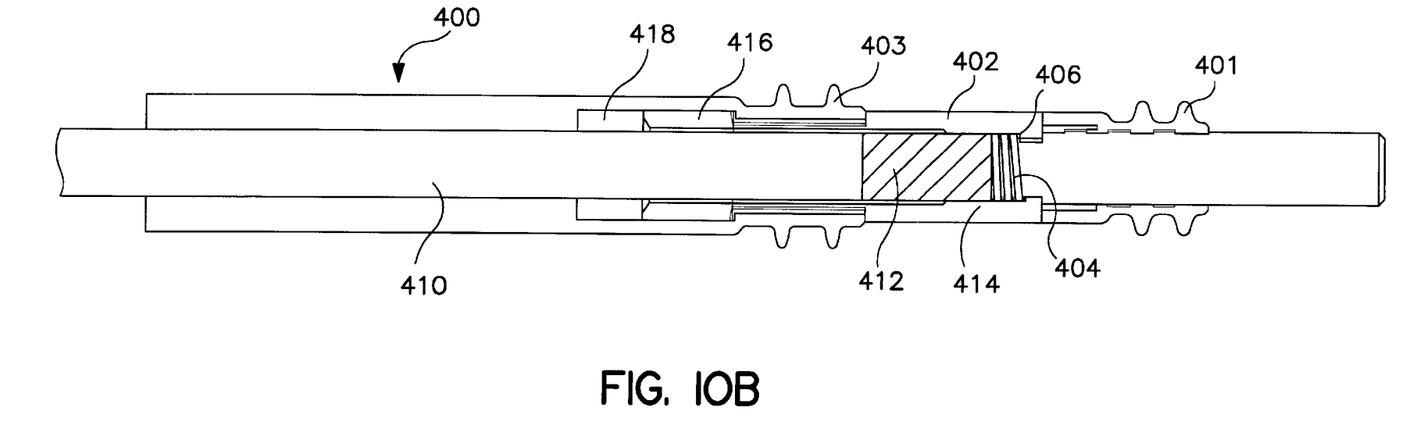
FIG. 10B is a side cutaway view of the embodiment of FIG. 10A illustrating the manner in which the spring coil compresses when the lead is fully inserted within the up-sizing sleeve.

FIG. 10B is a side cutaway view of the embodiment of FIG. 10A illustrating the manner in which the spring coil 404 compresses when the lead is fully inserted within the up-sizing sleeve 400.

It may be noted that the inventive system and method of coupling a lead to a medical device as described and illustrated herein may be adapted for use with any size lead, any type of connector standard, and any type of medical device. For example, the up-sizing sleeve may be used with leads for drug delivery devices, devices adapted for neurological applications, or for any other type of physiological application requiring a lead coupled to an implantable or non-implantable device. Thus, many adaptations of the above-described invention will become apparent to one skilled in the art, and the description is therefore to be considered not as limiting, but as exemplary only. Additional scopes and aspects of the invention are described in attached Appendix A which is incorporated herein by reference in its entirety.

What is claimed is:

1. A system for coupling a proximal end of a medical electrical lead to a medical device, comprising:
    a connector pin terminating the proximal end of the lead and having a predetermined diameter; and
    an up-sizing sleeve having an internal surface and an external surface, a distal opening, and a proximal opening, one or more interior sealing rings, and one or more relatively rigid support members extending along the internal surface; wherein
    the internal surface forms a lumen to engage the proximal end of the lead;
    the external surface conforms to predetermined dimensions when the proximal end of the lead is engaged within the lumen of the up-sizing sleeve;
    the distal opening receives the proximal end of the lead into the lumen;
    the connector pin extends proximally beyond the proximal opening, for a predetermined length, when the proximal end of the lead is engaged within the lumen of the up-sizing sleeve;
    the one or more interior sealing rings provide a fluid tight seal with the proximal end of the lead engaged within the lumen of the up-sizing sleeve; and
    the one or more support members prevent deformation in order to maintain the predetermined dimensions of the external surface of the up-sizing sleeve when the proximal end of the lead is engaged within the lumen of the up-sizing sleeve.

2. The system of claim 1 wherein the predetermined diameter of the connector pin, the predetermined length of the connector pin, extending proximally beyond the proximal opening of the up-sizing sleeve, and the predetermined dimensions of the external surface of the up-sizing sleeve, all conform to an industry standard.

3. The system of claim 1, further comprising:
    a connector ring being disposed about the proximal end of the lead and offset distally from the connector pin; and
    a conductive ring member having an outer surface and an inner surface and being disposed about the up-sizing sleeve along the one or more support members and offset distally from the proximal opening of the sleeve; wherein
    the outer surface of the conductive ring member forms a portion of the external surface of the up-sizing sleeve and the inner surface of the conductive ring member defines a means for electrically engaging the connector ring of the medical electrical lead.

4. The system of claim 3 wherein the upsizing sleeve further comprises a relatively flexible and generally tubular member; wherein the tubular member includes a first portion and a second portion and the inner surface of the conductive ring member includes channels; wherein the conductive ring member is positioned between the first portion and the second portion of the tubular member and the first portion is coupled to the second portion via the channels.

5. The system of claim 3 wherein the means for electrically engaging the connector ring of the medical electrical lead includes conductive teeth being formed in the inner surface of the conductive ring member.

6. The system of claim 3 wherein the means for electrically engaging the connector ring of the medical electrical lead includes a multi-beam connector being housed within the inner surface of the conductive ring member.

7. The system of claim 3 wherein
the connector ring of the lead includes a lip;
the inner surface of the conductive ring member of the up-sizing sleeve includes a shoulder; and
the means for electrically engaging the connector ring includes a spring coil member; the spring coil member having a proximal end and a distal end, and being housed within the inner surface of the conductive ring member and oriented along a longitudinal axis of the up-sizing sleeve; the proximal end of the spring coil member coupled to the shoulder and the distal end of the spring coil engaging the connector ring of the lead via the lip.

8. The system of claim 3 wherein the up-sizing sleeve further includes a first portion and a second portion; the first portion and the second portion being adapted to come together in a snap-fit joint; wherein
the conductive ring member is an integral part of the first portion and includes a distal edge;
the means for electrically engaging the connector ring of the medical electrical lead is an integral part of the second portion and includes deformable members adapted to slide under the distal edge of the conductive ring member for the snap-fit joint within the inner surface of the conductive ring member.

9. The system of claim 3 wherein the conductive ring member of the up-sizing sleeve includes a mechanical coupling means being adapted to rigidly couple the up-sizing sleeve to the connector ring of the lead.

10. The system of claim 3 wherein the one or more interior sealing rings are further defined by one or more grommets; the one or more grommets being housed within the one or more support members of the up-sizing sleeve.

11. The system of claim 3 further comprising a hub, an offset leg having a proximal portion being terminated in a pin, and a high voltage coil conductor; wherein
the offset leg is joined, via the hub, to the up-sizing sleeve in proximity to the distal opening of the up-sizing sleeve; and
the pin is electrically connected to the conductive ring member of the upsizing sleeve via the high voltage coil conductor.

12. The system of claim 11 wherein the proximal portion of the offset leg conforms to an industry standard.

13. The system of claim 1 further comprising one or more grooves being formed in the proximal end of the lead and one or more lips being formed on the internal surface of the up-sizing sleeve; wherein the one or more grooves are located to engage the one or more lips when the proximal end of the lead is engaged within the lumen of the up-sizing sleeve and the connector pin extends proximally beyond the proximal opening, for a predetermined length.

14. The system of claim 1 further comprising one or more grooves being formed in the proximal end of the lead; wherein the one or more grooves are located to engage the one or more sealing rings when the proximal end of the lead is engaged within the lumen of the up-sizing sleeve and the connector pin extends proximally beyond the proximal opening, for a predetermined length.

15. The system of claim 1 wherein the upsizing sleeve further comprises a relatively flexible and generally tubular member having a reinforcing member positioned in proximity to the distal opening of the sleeve; wherein the reinforcing member limits flexural stress of the proximal end of the lead when the proximal end of the lead is engaged within the lumen of the up-sizing sleeve.

16. The system of claim 1 further comprising a means to aid in inserting the proximal end of the lead into the lumen of the up-sizing sleeve.

17. The system of claim 16 wherein the means to aid in inserting the proximal end of the lead into the lumen of the up-sizing sleeve includes a pull-wire device; the pull-wire device having an elongated member being adapted to pull the proximal end of a medical electrical lead into the lumen of the up-sizing sleeve.

18. The system of claim 16 wherein the means to aid in inserting the proximal end of the lead into the up-sizing sleeve includes a tubular member having a lubricious surface; wherein the tubular member is inserted into the distal opening of the up-sizing sleeve and the proximal end of the lead is inserted into the lumen of the up-sizing sleeve via the tubular member.

\* \* \* \* \*